(12) United States Patent
Eifler

(10) Patent No.: US 10,675,426 B2
(45) Date of Patent: Jun. 9, 2020

(54) MASK CUSHION FOR A FULL FACE MASK

(71) Applicant: WEINMANN GERAETE FUER MEDIZIN GMBH + CO. KG, Hamburg (DE)

(72) Inventor: Martin Eifler, Glueckstadt (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 1033 days.

(21) Appl. No.: 14/855,699

(22) Filed: Sep. 16, 2015

(65) Prior Publication Data

US 2016/0082213 A1    Mar. 24, 2016

(30) Foreign Application Priority Data

Sep. 23, 2014   (DE) .................. 10 2014 013 796

(51) Int. Cl.
*A61M 16/06*    (2006.01)

(52) U.S. Cl.
CPC .... *A61M 16/0622* (2014.02); *A61M 16/0616* (2014.02); *A61M 16/0644* (2014.02); *A61M 2016/0661* (2013.01); *A61M 2205/0216* (2013.01)

(58) Field of Classification Search
CPC .......... A61M 16/0605; A61M 16/0611; A61M 16/0616; A61M 16/0622; A61M 2016/0661; A61M 16/06
See application file for complete search history.

(56) References Cited

U.S. PATENT DOCUMENTS

| | | | | |
|---|---|---|---|---|
| 6,789,543 | B2 * | 9/2004 | Cannon ............ | A61M 16/0683 128/206.18 |
| 6,796,308 | B2 * | 9/2004 | Gunaratnam ........ | A61M 16/06 128/206.24 |
| 7,882,837 | B2 * | 2/2011 | Kwok .................. | A61M 16/06 128/112.1 |
| 2002/0100479 | A1 * | 8/2002 | Scarberry ............ | A61M 16/06 128/206.24 |
| 2004/0094157 | A1 * | 5/2004 | Dantanarayana .... | A61B 5/0876 128/206.21 |
| 2006/0201514 | A1 * | 9/2006 | Jones .................... | A61M 16/06 128/206.21 |
| 2008/0110464 | A1 * | 5/2008 | Davidson .............. | A61M 16/06 128/206.26 |
| 2008/0149104 | A1 * | 6/2008 | Eifler .................... | A61M 16/06 128/206.24 |
| 2009/0107506 | A1 * | 4/2009 | Collazo ................ | A61M 16/06 128/206.21 |
| 2010/0006100 | A1 * | 1/2010 | Eifler .................... | A61M 16/06 128/206.24 |
| 2011/0315143 | A1 | 12/2011 | Frater | |
| 2013/0008448 | A1 * | 1/2013 | Todd .................... | A61M 16/06 128/205.25 |

(Continued)

FOREIGN PATENT DOCUMENTS

| | | |
|---|---|---|
| DE | 10002571 A1 | 7/2001 |
| EP | 2737921 A2 | 6/2014 |
| WO | 2010111749 A1 | 10/2010 |

*Primary Examiner* — Michael J Tsai
(74) *Attorney, Agent, or Firm* — Abel Schillinger, LLP

(57) ABSTRACT

Disclosed is a mask cushion for a full face mask with a single sealing lip for sealing contact with the face of a user.

20 Claims, 5 Drawing Sheets

(56) References Cited

U.S. PATENT DOCUMENTS

2013/0014760 A1* 1/2013 Matula, Jr. ............ A61M 16/06
  128/205.25
2014/0144448 A1   5/2014 Eifler
2014/0216462 A1   8/2014 Law et al.
2014/0352134 A1* 12/2014 Ho ........................ A61M 16/06
  29/592

* cited by examiner

Fig. 1b
Fig. 1a
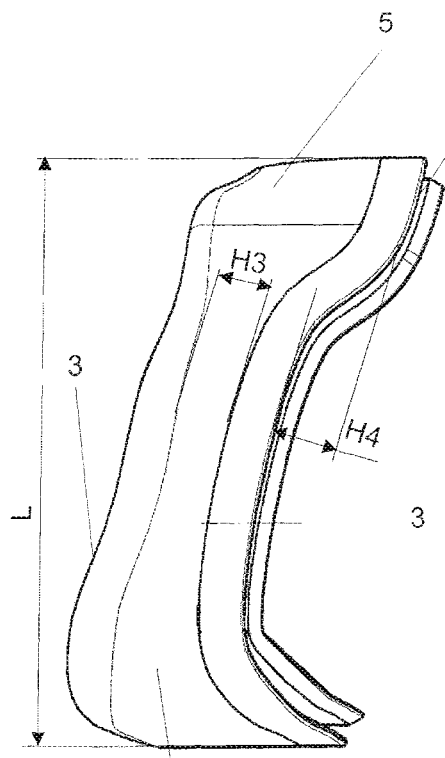
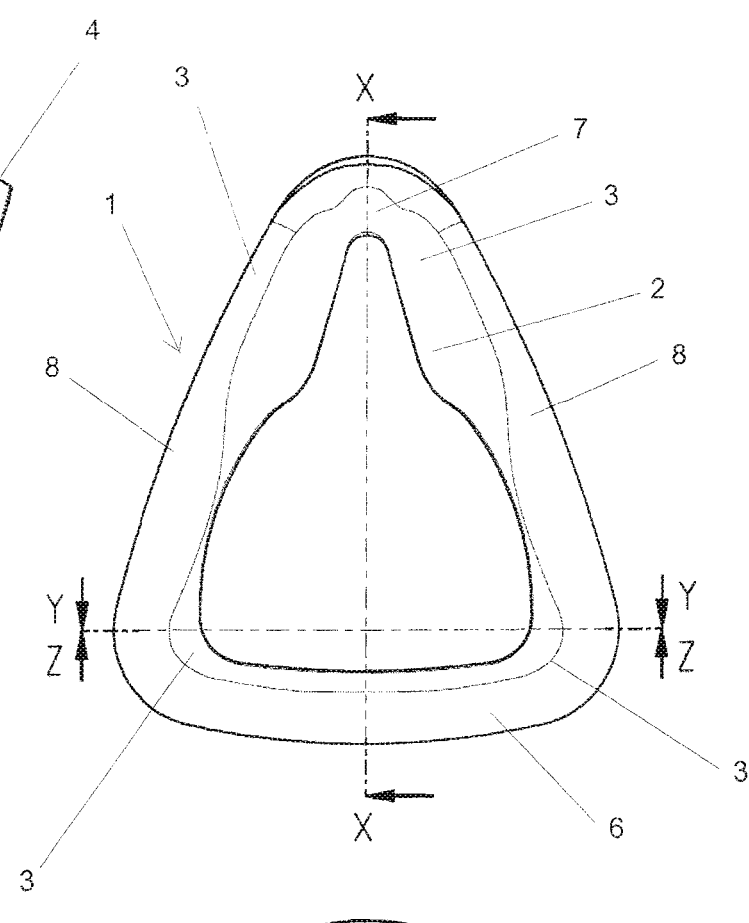
Fig. 1c
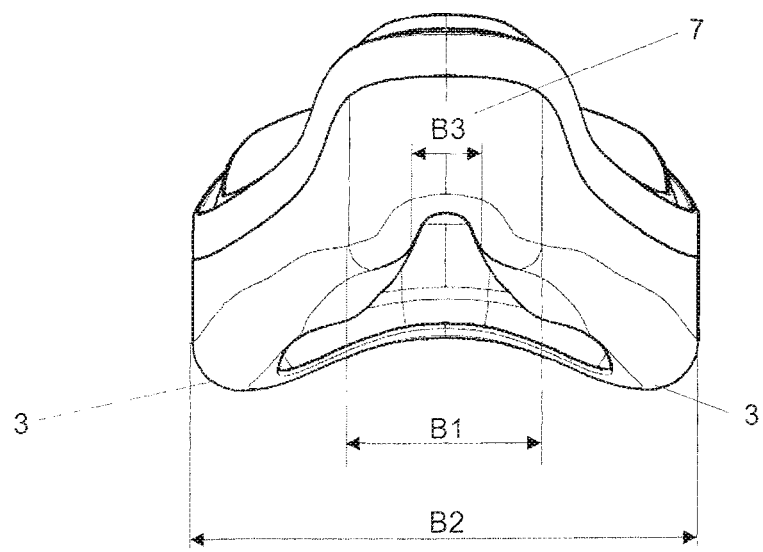

a)

b)

MASK CUSHION FOR A FULL FACE MASK

CROSS-REFERENCE TO RELATED APPLICATIONS

The present application claims priority under 35 U.S.C. § 119 of German Patent Application No. 10 2014 013 796.1, filed Sep. 23, 2014, the entire disclosure of which is expressly incorporated by reference herein.

BACKGROUND OF THE INVENTION

1. Field of the Invention

The present invention relates to a mask cushion for a full face mask.

2. Discussion of Background Information

Masks are used in the area of respiration and sleep therapy for supplying a patient with respiratory gas by means of a flow or pressure source. The mask represents the interface between patient and appliance. It consists of a mask body with a cushion and is mostly fixed on the patient's head by means of a harness and an additional forehead support. The mask body is generally made of a relatively stiff plastic, and the cushion, which bears on the face of the patient, is made of a relatively thin, soft material, preferably a skin-compatible silicone, a thermoplastic elastomer (TPE) or polyurethane, and it generally has a sealing lip in order to ensure a sufficient seal and to prevent leaks. These masks may be designed as nasal masks or full face masks (or also mouth and nose masks).

Conventional masks are usually available in the sizes S, M and L, so as to meet the greatest possible number of different configurations of the face and nose of the patients, and so as to ensure the greatest possible wearing comfort, the best possible fit, and a high degree of leak-tightness.

Known solutions of this kind mean that a large number of masks have to be offered in order to cover all different shapes and sizes of faces. "Universal masks" in a universal size are known from the area of nasal masks. Full face masks in only one size which are suitable for a large number of face shapes and sizes are not known. This is due to the fact that the variability in the distance between the nose and lower lip or chin is large. Moreover, noses of different sizes must also be considered.

In view of the foregoing, it would be advantageous to have available a mask cushion for full face masks which provides a high degree of adaptability to different sizes and different shapes of face parts, nose parts and chin parts of the patients. Patients can have different face shapes and sizes, with different nose shapes with high or low nose bridge areas, narrow or broad and long or short noses. The mouth and chin areas may likewise be formed very differently in size and shape, for which reason the mask cushion should be able to adapt to all possible face shapes and sizes, and to provide the desired fit and leak-tightness.

SUMMARY OF THE INVENTION

The present invention provides a mask cushion for a full face mask having only one sealing lip, a sealing area facing the patient's face and leading into the sealing lip, a contact area to the mask body, and a deformation area which extends between the contact area and the sealing area. The deformation area has a first height (H1) at the base at the bottom, a second height (H2) at the top in the nose bridge area, and a third height (H3) laterally in the paranasal area, the first height (H1) being at least twice as high as the third height (H3).

In one aspect of the mask cushion of the present invention, the first height (H1) may be greater than the second height (H2), and the second height may be greater than the third height (H3).

In another aspect of the mask cushion, the deformation area may be 25 mm+/−3 mm high (H1) at the bottom at the base and/or 20 mm+/−2.5 mm high (H2) at the top in the nose bridge area and/or 11 mm+/−2 mm (H3) laterally in the paranasal area.

In yet another aspect, the mask cushion may be made of an elastomeric plastic and may have at least two different wall thicknesses.

In a still further aspect, the wall thickness in the deformation area at the bottom at the base (W2) and the top in the nose bridge area (W1) may be thinner than laterally in the paranasal area (W3).

In another aspect, the wall thickness in the deformation area in the nose bridge area (W1) may be thinner than the wall thickness in the deformation area at the base (W2), and the wall thickness (W2) may be thinner than laterally in the paranasal area (W3).

In another aspect, the wall thickness (W3) may be at least twice as thick as the wall thickness (W2).

In another aspect, the length (L) may be 105 mm+/−6 mm and the width (B2) may be 90 mm+/−4 mm.

In another aspect of the mask cushion of the instant invention, the outer width in the nose bridge area (B1) may be 3×, preferably 4×, wider than in the inner section of the nose area (B3).

In another aspect of the mask cushion, the outer width in the nose area (B1) may be 35 mm+/−3 mm, and may be 8 mm+/−2 mm in the inner section of the nose area (B3).

In another aspect of the mask cushion of the present invention, the wall thickness (W1) in the nose bridge area may be ≤0.6 mm. For example, the wall thickness (W1) in the nose bridge area may be in the range of 0.2-0.5 mm.

In another aspect of the mask cushion, the side area may have a wall thickness (W3) in the range of 1.2-2.9 mm. For example, the side area may have a wall thickness (W3) in the range of 1.5-2.5 mm, preferably 2.1 mm+/−2 mm.

In another aspect of the mask cushion, the wall thickness W2 may continuously decrease from the base toward W4.

The present invention also provides a full face mask which comprises the mask cushion of the present invention as set forth above, including the various aspects thereof.

In one aspect thereof, the full face mask may comprise a steplessly adjustable forehead support. For example, the steplessly adjustable forehead support may be adjusted by the tightening force of the head harness. In another aspect, the forehead support may comprise a spring element.

BRIEF DESCRIPTION OF THE DRAWINGS

Further advantages and features of the present invention can be found in the description of the exemplary embodiments which are set forth below with reference to the attached Figures. The Figures show:

FIG. 1a: mask cushion in top view
FIG. 1b: mask cushion in side view
FIG. 1c: mask cushion from above

DETAILED DESCRIPTION OF EMBODIMENTS

Figure 2A:
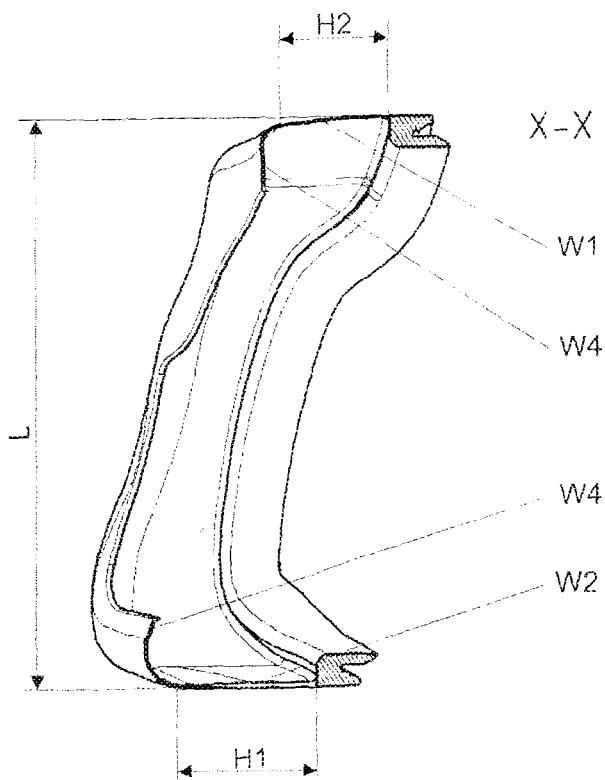
FIG. 2a: vertical sectional view along the plane x/x

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawing making apparent to those of skill in the art how the several forms of the present invention may be embodied in practice.

FIG. 1 shows the mask cushion in a top view. A vertical sectional plane x and a horizontal sectional plane y/z are indicated. The sections are illustrated in FIG. 2. The cushion has a nose bridge area (7), side areas (8), the base area (6) and the sealing area (3) toward the patient. The side areas (8) extend from the contact area to the mask body (4) substantially vertically upward. The sealing area (3) leads into a single sealing lip (2), which is formed integrally onto the other areas and on the inside frees an opening which serves for the introduction of at least the nose and mouth of the patient. The sealing area (3) extends away from the side areas and the base area and also from the nose bridge area to the opening, wherein the sealing area (3) extends at least partially horizontally to the side area (8). A deformation area (5) extends between the contact area (4) and the sealing area (3). In the side area (8), however, the deformation area (5) is rather a support area through the use of a higher wall thickness. In the sense of the invention as embodied here, the contact area (4) may be designed as a mechanical connection to a hard part of the mask body or may also be designed to transfer directly to the hard part of the mask body, for example as a two-component connection or adhesive connection.

FIG. 1b shows the cushion in a side view. The contact area (4) has a strong indentation with the height (H4). In comparison to the side view of the cushion of the prior art in FIG. 3, it can clearly be seen that H4 is much less pronounced in the prior art. The strong indentation of height H(4) in the mask cushion according to the invention serves to provide the shortest and most stable possible deformation area (5) in the side area (8) of the cushion. The maximum length (L) of the cushion is 105 mm+/−6 mm and the maximum width (B2) is 90 mm+/−4 mm.

FIG. 1c shows the cushion in a top view. The width of the nose bridge area (B1) was chosen to be wider than in known masks, in order to ensure an optimal fit and leaktightness even with wider and flatter nose shapes. Through the chosen geometry, the cushion sits lower on the nose of the user. With the chosen contour, a higher nose bridge dips deeper into the cushion. The outer width in the nose bridge area (B1) is at least 3×, preferably 4×, wider than in the inner section of the nose area (B3). B2 represents the maximum width of the cushion.

FIG. 2a shows the cushion sectioned in the plane x. The patient is most sensitive in the nose bridge area (7), for which reason a very thin wall (W1) is chosen here that measures ≤0.6 mm, preferably 0.2-0.5 mm, particularly preferably 0.25 mm. This area can be easily deformed and adapted to the shape of the nose. The wall of the sealing lip (W4) may have the same thickness as the wall W1, or it may also be thicker. The thickness W1 would then be 0.4 mm and W4 0.5 mm.

The base area (6) having the wall thickness (W2) is likewise designed thinly in contrast to the side areas (8) having the wall thicknesses (W3), in order to achieve the greatest possible flexibility for the chin area. The wall thickness (W2) is in the range of 0.5-1.2 mm, preferably 1.0 mm. Since the patient is the least sensitive to the contact points in the side area (8) of the cushion, the wall thicknesses (W3) of this area may be more thickly designed and thus ensure the rigidity and support strength of the cushion. The wall thickness (W3) in this area is 1.2-2.9 mm, preferably 1.5-2.5 mm, particularly preferably 2.1 mm. The sealing lip is designed as a single sealing lip. The wall thickness W4 of the sealing lip was designed around its complete circumference with a nearly uniform, thin wall thickness (W4) of 0.2-0.75 mm, preferably 0.5 mm, which allows the patient a comfortable fit.

The height (H2), as measured in the area of the wall thickness (W1) from the contact area (4) to the radius, is 18-25 mm in the nose bridge area, preferably 20-25 mm, particularly preferably 20 mm+/−2.5 mm, and is higher than in masks of the prior art. Thus, a wide range is opened with good sealing properties for various nose bridges.

The height (H1) of the base area (6) is higher than in commercially available mask cushions and is in the range of 23-28 mm, preferably 25 mm+/−3 mm, particularly preferably 25 mm+/−2 mm.

It is clear from FIG. 1 and FIG. 2 that the specified heights H1, H2 and H3 refer to the deformation area (5). This extends between the outer edge of the contact area (4) and the transition to the sealing area (3). More specifically, starting from the outer edge of the contact area (4), i.e. above the thickened zone, up to the start of the radius which transitions into the sealing area (3).

Figure 2B:
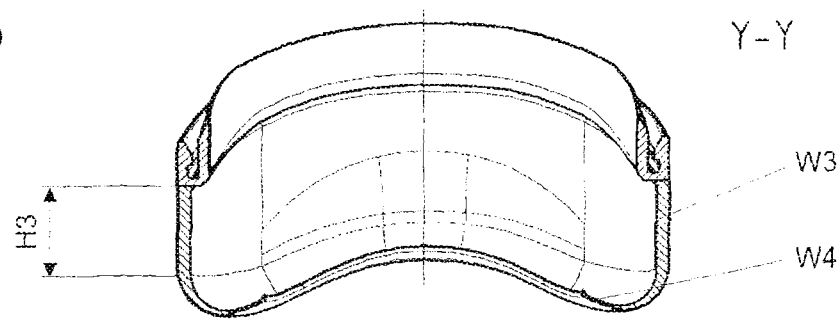
FIG. 2b: horizontal sectional view along the plane y/y

FIG. 2b shows the cushion sectioned in the plane y. The height (H3) of the side area (8) is less than in commercially available mask cushions and is in the range of 8-13 mm, preferably 11 mm+/−2 mm. The deformation area (5) has a first height (H1) at the bottom at the base, a second height (H2) at the top in the nose bridge area (7), and a third height (H3) laterally in the paranasal area (8), wherein the first height (H1) is greater than the second height (H2) and the second height is greater than the third height (H3), and wherein the first height (H1) is at least twice as high as the third height (H3).

Figure 2C:
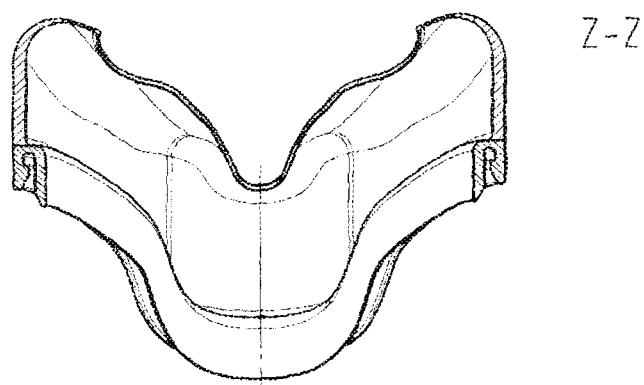
FIG. 2c: horizontal sectional view along the plane z/z

FIG. 2c shows the cushion sectioned in the plane z.

Figure 3:
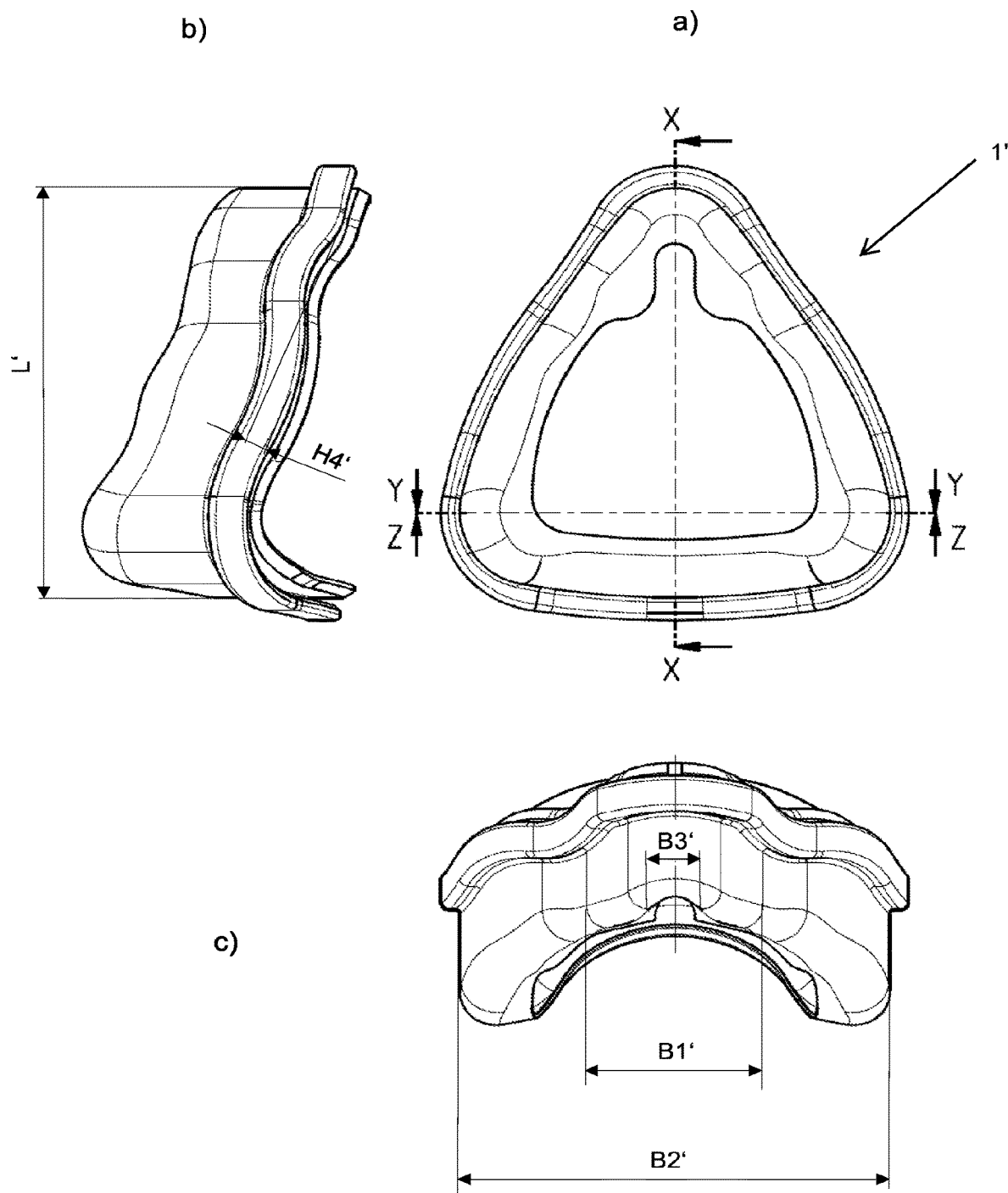
FIG. 3: comparison of invention to the prior art

In FIG. 3, the differences between the mask cushion (M) according to the invention and cushions from the prior art (M') are clear in the perspective view. In particular, it is clearly evident that the height H4' is lower in the prior art, and the width BF is greater. According to the invention, H4 is in the range of 10-14 mm, preferably greater than 11 mm. H4' in the prior art is in a range of less than 8 mm.

Figure 4:
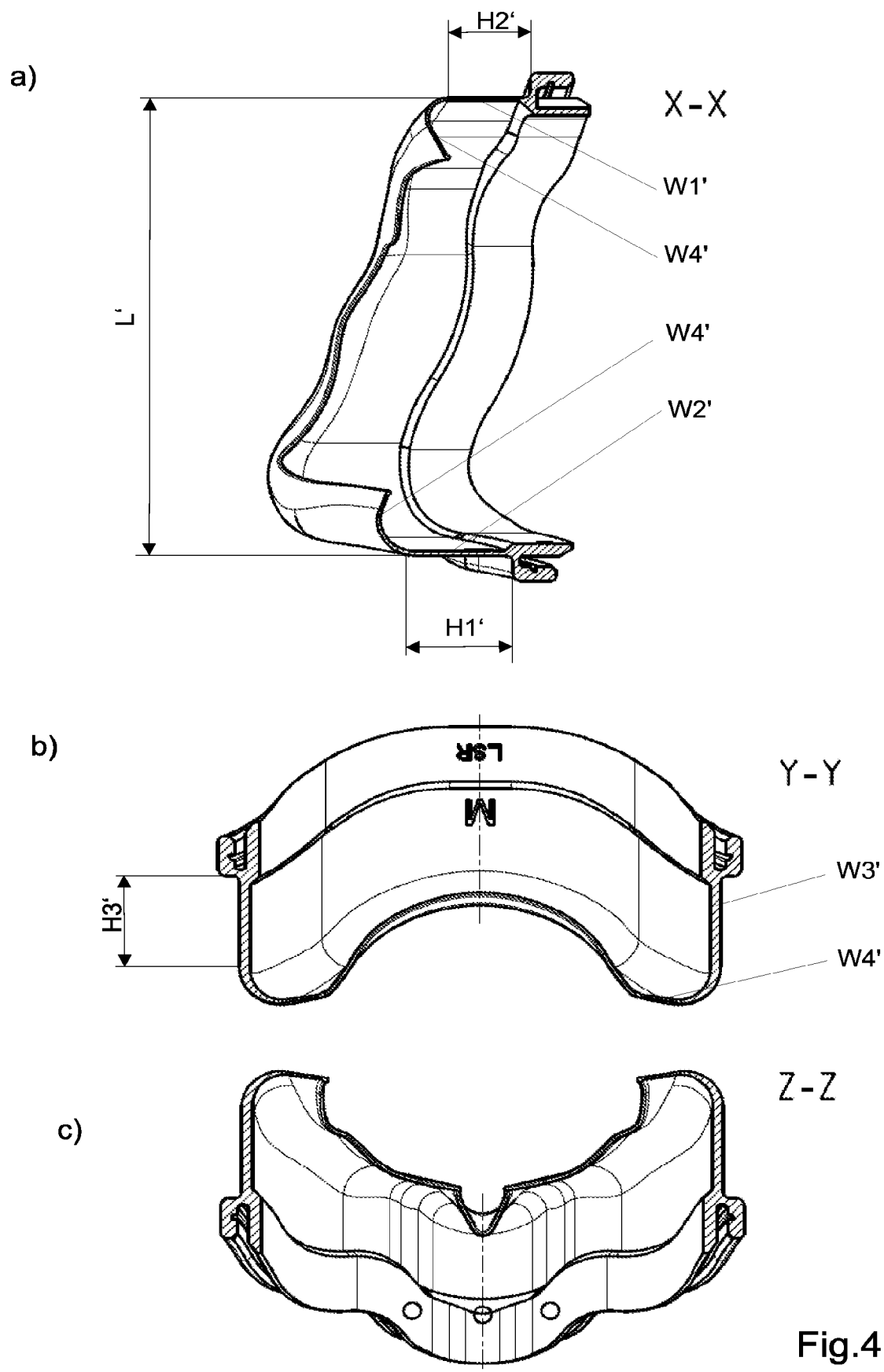
FIG. 4: comparison of invention to the prior art in various views
Figure 5:
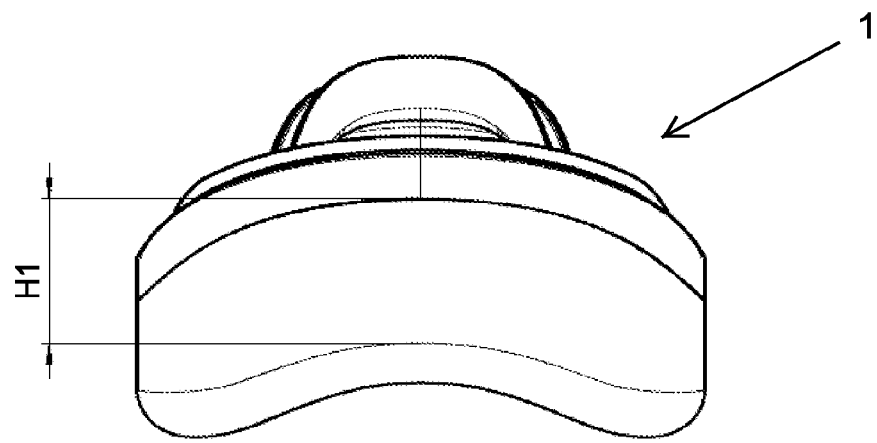
FIG. 5: comparison of invention to the prior art in sectional views
Figure 5:
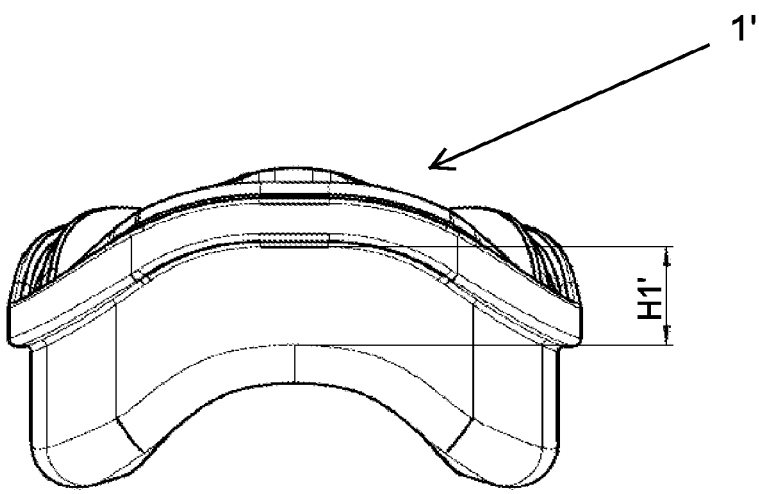

FIG. 4 and FIG. 5 show differences of the mask cushion (M) according to the invention compared to cushions of the prior art (M').

A comparison of the mask cushion (M) to the cushions of the prior art (M') makes clear the difference of the invention.

The key features of the cushion according to the invention are the very large deformation area of the nose bridge area (1), which is achieved by means of the suitable choice of the wall thickness (W1) and width (B1) with respect to the width B3 and height (H2). This area is crucial for the adaptability to different sizes and different shapes of nose parts of the patients. Furthermore, in the cushion according to the invention, the wall thickness (W2) at the base, the height at the base (H1), as well as the wall thickness (W3) at the side, the height at the side (H3), are crucial for a large adaptability at the base and a high support function in the side area (8).

The wall thickness (W2') is 1 mm; (W1') is 0.5 mm; (W3') is 1.5 mm; W4' is 0.5 mm. The wall thickness (W3') is thus not twice as thick as the wall thickness (W2').

It is clear from the comparison of the invention with the prior art (see FIGS. 3 to 5) that, in the cushion according to the invention, H1 is greater than H1'; H3 is smaller than H3'; H4 is greater than H4'; W2 is smaller than W2'. At the sides (8), the cushion according to the invention is approximately ⅓ flatter with respect to H3 than cushions according to the prior art, thereby achieving a stable edge for better support at the sides of the nose.

It is therefore necessary that the mask body is higher in the side area, which results in a pronounced height H4 (of approximately 12 mm).

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A mask cushion for a full face mask, wherein the mask cushion comprises only one sealing lip, a sealing area adapted for facing a patient's face and leading into the sealing lip, a contact area to a mask body, and a deformation area which extends between the contact area and the sealing area, the deformation area having a first height (H1) at a base at the bottom, a second height (H2) at the top in a nose bridge area, and a third height (H3) laterally in a paranasal area, with the first height (H1) being at least twice as high as the third height (H3).

2. The mask cushion of claim 1, wherein the first height (H1) is greater than the second height (H2), and the second height is greater than the third height (H3).

3. The mask cushion of claim 1, wherein H1 is 25 mm+/−3 mm high and/or H2 is 20 mm+/−2.5 mm high.

4. The mask cushion of claim 1, wherein the mask cushion is made of an elastomeric plastic and has at least two different wall thicknesses.

5. The mask cushion of claim 1, wherein a wall thickness in the deformation area at the base and in the nose bridge area is thinner than laterally in the paranasal area.

6. The mask cushion of claim 1, wherein a wall thickness in the deformation area in the nose bridge area is thinner than a wall thickness in the deformation area at the base, and a wall thickness at the base is thinner than laterally in the paranasal area.

7. The mask cushion of claim 1, wherein a wall thickness laterally in the paranasal area is at least twice a wall thickness in the deformation area at the base.

8. The mask cushion of claim 1, wherein a maximum length of the cushion is 105 mm+/−6 mm and a maximum width of the cushion is 90 mm+/−4 mm.

9. The mask cushion of claim 1, wherein an outer width in a nose bridge area is three times wider than in an inner section of the nose area.

10. The mask cushion of claim 1, wherein an outer width is 35 mm+/−3 mm in a nose area, and 8 mm+/−2 mm in an inner section of the nose area.

11. The mask cushion of claim 1, wherein a wall thickness in the nose bridge area is ≤0.6 mm.

12. The mask cushion of claim 11, wherein the wall thickness in the nose bridge area ranges from 0.2 mm to 0.5 mm.

13. The mask cushion of claim 1, wherein a wall thickness of a paranasal side area ranges from 1.2 mm to 2.9 mm.

14. The mask cushion of claim 13, wherein the wall thickness in the paranasal side area ranges from 1.5 mm to 2.5 mm.

15. The mask cushion of claim 13, wherein the wall thickness in the paranasal side area is 2.1 mm+/−0.2 mm.

16. The mask cushion of claim 1, wherein the wall thickness in the deformation area continuously decreases from the base toward a wall of the sealing lip.

17. The mask cushion of claim 1, wherein a wall thickness (W4) of the sealing lip is 0.2-0.75 mm and designed substantially uniformly around its complete circumference.

18. A full face mask, wherein the mask comprises the mask cushion of claim 1.

19. The full face mask of claim 18, wherein the mask further comprises a steplessly adjustable forehead support.

20. The full face mask of claim 18, wherein the mask further comprises a forehead support which comprises a spring element.

* * * * *